United States Patent
Yamashita et al.

(10) Patent No.: US 7,372,053 B2
(45) Date of Patent: May 13, 2008

(54) ROTATING GANTRY OF PARTICLE BEAM THERAPY SYSTEM

(75) Inventors: Tsutomu Yamashita, Hitachi (JP); Shigeji Kaneko, Hitachi (JP); Yutaka Muramatsu, Tokai (JP); Hiroshi Saga, Takahagi (JP)

(73) Assignees: Hitachi, Ltd., Tokyo (JP); Hitachi Setsubi Engineering Co., Ltd., Ibaraki (JP)

( * ) Notice: Subject to any disclaimer, the term of this patent is extended or adjusted under 35 U.S.C. 154(b) by 261 days.

(21) Appl. No.: 11/359,484

(22) Filed: Feb. 23, 2006

(65) Prior Publication Data

US 2006/0192072 A1  Aug. 31, 2006

(30) Foreign Application Priority Data

Feb. 25, 2005  (JP)  ............................. 2005-050062

(51) Int. Cl.
*A61N 5/01* (2006.01)
*A61N 5/10* (2006.01)

(52) U.S. Cl. .............. 250/492.3; 250/398; 250/492.21; 600/1

(58) Field of Classification Search ............. 250/492.3, 250/398, 397; 600/1; 378/132, 19, 17
See application file for complete search history.

(56) References Cited

U.S. PATENT DOCUMENTS

| | | | | |
|---|---|---|---|---|
| 4,093,861 A | * | 6/1978 | Kelman et al. ................ 378/17 |
| 4,093,862 A | * | 6/1978 | Brandt et al. .................. 378/17 |
| 4,112,303 A | * | 9/1978 | Brandt .......................... 378/17 |
| 4,115,695 A | * | 9/1978 | Kelman ......................... 378/17 |
| 4,917,344 A | | 4/1990 | Prechter et al. | |
| D323,386 S | * | 1/1992 | Perusek ..................... D24/159 |
| 5,993,373 A | * | 11/1999 | Nonaka et al. ................ 600/1 |
| 6,752,472 B2 | * | 6/2004 | Bezzina ......................... 303/7 |
| 7,049,917 B2 | * | 5/2006 | Sano et al. ................. 335/255 |
| 7,300,118 B2 | * | 11/2007 | Hoover et al. ................. 303/3 |
| 2004/0061077 A1 | * | 4/2004 | Muramatsu et al. ..... 250/492.3 |
| 2004/0061078 A1 | * | 4/2004 | Muramatsu et al. ..... 250/492.3 |
| 2004/0111134 A1 | * | 6/2004 | Muramatsu et al. .......... 607/88 |

(Continued)

FOREIGN PATENT DOCUMENTS

EP    1 402 923 A1    3/2004

(Continued)

OTHER PUBLICATIONS

Copy of European Search Report dated Feb. 27, 2007.

*Primary Examiner*—Nikita Wells
*Assistant Examiner*—Johnnie L Smith, II
(74) *Attorney, Agent, or Firm*—Dickstein Shapiro LLP

(57) ABSTRACT

A rotating gantry includes a link frame for supporting a plurality of rollers which rotatably support the rotating gantry, a brake for releasing a braking force applied to at least one of the rollers upon supply of air and applying the braking force to the one roller upon discharge of air, and a solenoid valve for sealing the supplied air in the brake when closed, and discharging the air from the brake when opened. The solenoid valve is supported by a solenoid valve support member mounted to the link frame such that the solenoid valve is positioned just near the brake. The rotating gantry can be more quickly braked and stopped while maintaining high irradiation accuracy.

12 Claims, 11 Drawing Sheets

U.S. PATENT DOCUMENTS

| | | | |
|---|---|---|---|
| 2005/0061996 A1* | 3/2005 | Yanagisawa et al. | 250/492.3 |
| 2006/0163495 A1* | 7/2006 | Hiramoto et al. | 250/492.3 |
| 2006/0284479 A1* | 12/2006 | Hoover et al. | 303/89 |
| 2007/0023699 A1* | 2/2007 | Yamashita et al. | 250/492.21 |
| 2007/0215819 A1* | 9/2007 | Hiramoto et al. | 250/492.3 |

FOREIGN PATENT DOCUMENTS

| | | |
|---|---|---|
| GB | 1 036 348 A | 7/1966 |
| GB | 2 077 211 A | 12/1981 |
| JP | 11 216195 | 8/1999 |
| WO | WO 02/066852 A1 | 8/2002 |

* cited by examiner

COMPARATIVE EXAMPLE

COMPARATIVE EXAMPLE

INVENTION

INVENTION

COMPARATIVE EXAMPLE

INVENTION

ROTATING GANTRY OF PARTICLE BEAM THERAPY SYSTEM

BACKGROUND OF THE INVENTION

1. Field of the Invention

The present invention relates to a rotating gantry of a particle beam therapy system, and more particularly to a rotating gantry suitable for use in a particle beam therapy system for irradiating an ion beam, such as a proton or carbon ion beam, to an affected part of the patient body for treatment.

2. Description of the Related Art

There is known a therapy method of setting an isocenter (irradiation target center) to an affected part of the patient body, e.g., a cancer, and irradiating an ion beam, such as a proton or carbon ion beam, to the affected part. A particle beam therapy system for use with that therapy method comprises, for example, an ion beam generator, a beam line, and an irradiation device installed in a rotating gantry. The ion beam accelerated in the ion beam generator reaches the irradiation device through the beam line and is irradiated to the affected part of the patient body from the irradiation device. At that time, the irradiation device is rotated around the patient body with rotation of the rotating gantry, thus enabling the ion beam to be irradiated to the affected part in accordance with the irradiation angle decided in a treatment plan.

Generally, the rotating gantry comprises a front ring, a rear ring, and a gantry barrel connecting the front ring and the rear ring by linear braces at plural points in the circumferential direction. The front ring and the rear ring are each supported by a plurality of rotatable rollers such that the rotating gantry is rotatable in the circumferential direction of the front ring and the rear ring. Reinforcing members of a truss structure are provided around the gantry barrel to which the irradiation device is mounted, to thereby provide a structure for increasing the strength of the gantry barrel. Further, the plurality of rollers are arranged along outer peripheral (circumferential) surfaces of the front ring and the rear ring by using link frames each made up of a parent link member rotatably attached to a bracket which is fixed to a pedestal, and two child link members rotatably coupled to the parent link member (see, e.g., Patent Document 1; U.S. Pat. No. 4,917,344).

SUMMARY OF THE INVENTION

In the known rotating gantry described above, although the reinforcing members of the truss structure are provided, the rigidity of the gantry barrel is not sufficient and three-dimensional swivel accuracy of the irradiation position during the irradiation of the ion beam from the irradiation device to the isocenter (i.e., isocenter accuracy) has a variation of about several millimeters with the rotation of the rotating gantry. Such a variation causes the problem that, prior to starting the irradiation for treatment, a lot of time is required for positioning of the patient body depending on an irradiation angle.

Against that background, a rotating gantry has recently been proposed in which the gantry barrel connecting the front ring and the rear ring has a cylinder structure. With such a rotating gantry, the rigidity of the gantry barrel can be increased and the variation of the isocenter accuracy can be suppressed to about 1 mm.

Although the proposed rotating gantry is able to improve the irradiation accuracy by increasing the rigidity of the gantry barrel by employing the cylinder structure, its weight is increased in comparison with the above-mentioned known rotating gantry including the gantry barrel made up of the plurality of braces and the reinforcing members of the truss structure. As a result, the inertial moment of the rotating gantry is increased and so is an emergency stop angle (i.e., an angle through which the rotating gantry is rotated from a time when emergency stop is instructed in a state rotating at the set speed to a time when a braking force from a brake is applied at 100%). The emergency stop is performed, for example, when the irradiation device is about to contact a treatment couch on which the patient is lying, etc. with malfunction of the rotating gantry, or when the condition of the patient is abruptly changed. From the viewpoint of safety, therefore, the emergency stop angle is preferably held comparable to that of the rotating gantry having the rigidity not yet increased. To that end, a response of the brake for applying the braking force to the rotating gantry has to be improved.

Though not disclosed in Patent Document 1, the plurality of rollers supporting the front ring and the rear ring generally include a driving roller connected to a motor to rotate the rotating gantry and a braking roller connected to the brake to perform, e.g., the emergency stop of the rotating gantry. The brake connected to the braking roller is usually provided with a failsafe structure capable of causing the braking force to safely act on the rotating gantry even when supply of source power is cut off. More specifically, when the rotating gantry is driven for rotation, air is supplied to the brake and a solenoid valve disposed outside the brake is closed, whereby the air is sealed in the brake. Accordingly, the braking force transmitted from the braking roller to the rotating gantry is released so that the rotating gantry can be rotated by the driving roller. On the other hand, in the event of the emergency stop, the solenoid valve disposed outside the brake is opened to discharge the air from the brake. Responsively, a gear member for actuating the braking roller is pressed by a spring disposed in the brake, whereby the braking force is applied from the braking roller to the rotating gantry.

In order to operate the brake having the above-described structure at a response as high as possible, the air has to be discharged from the brake as quick as possible. As a result of conducting various studies, the inventors have confirmed that the distance between the brake and the solenoid valve installed in the rotating gantry is the most important factor affecting delay of an air discharge time. In other words, the inventors have found that, in the known rotating gantries, because the brake and the solenoid valve are installed apart through a relatively long distance, a large amount of air is sealed in a line connecting the brake and the solenoid valve, and a long time is required to discharge the air. Thus, such installation layout has deteriorated the response of the brake and has prolonged a time until the braking force is fully applied.

An object of the present invention is to provide a rotating gantry of a particle beam therapy system, which can actuate braking in a shorter time.

To achieve the above object, the present invention provides a rotating gantry of a particle beam therapy system, the gantry comprising a gantry barrel; ring members provided respectively at axial opposite ends of the gantry barrel; a plurality of rollers rotatably supporting the ring members; a roller support member for supporting the plurality of rollers; a brake connected to at least one of the plurality of rollers, the brake releasing a braking force applied to the one roller upon supply of air and applying the braking force to the one roller upon discharge of air; a solenoid valve for sealing the supplied air in the brake when closed, and discharging the air from the brake when opened; and a solenoid valve support member mounted to the roller support member and supporting the solenoid valve.

In the rotating gantry of the present invention, the solenoid valve for supplying (sealing) and discharging air to and from the brake with opening and closing operations is supported by the solenoid valve support member mounted to the roller support member, whereby the solenoid valve can be positioned just near the brake. Therefore, an amount of air sealed in a line connecting the brake and the solenoid valve can be reduced, and the sealed air can be more quickly discharged from the brake. As a result, a response of the brake can be increased and a braking time of the rotating gantry can be cut. In particular, even when the rotating gantry has a larger mass due to rigidity increased for an improvement of irradiation accuracy, it is possible to brake and stop the rotating gantry in a shorter time.

According to the present invention, the rotating gantry of the particle beam therapy system can be braked and stopped in a shorter time.

DESCRIPTION OF THE PREFERRED EMBODIMENTS

One preferred embodiment of a rotating gantry of a particle beam therapy system will be described below with reference to the drawings.

Figure 1:
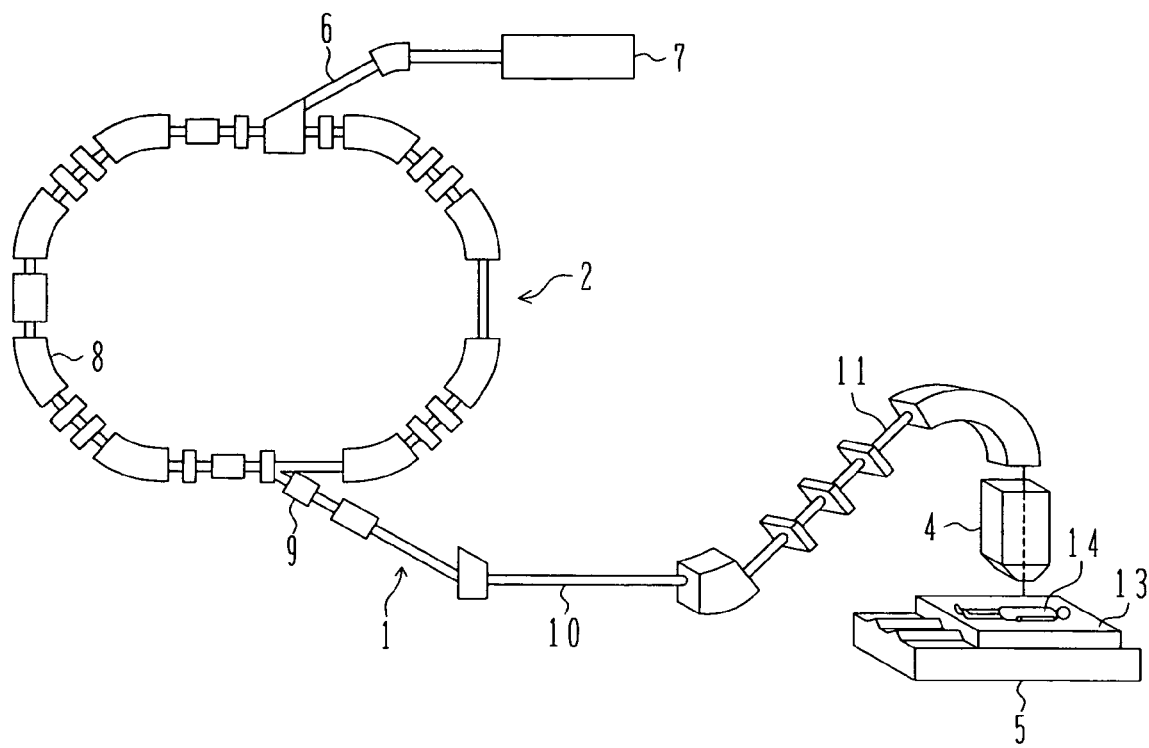
FIG. 1 is a schematic view showing the overall structure of a particle beam therapy system to which a rotating gantry according to a preferred embodiment of the present invention is applied.

The particle beam therapy system to which the rotating gantry according to the preferred embodiment is applied will be described below with reference to FIG. 1. The particle beam therapy system 1 comprises an ion beam generator 2, a rotating gantry 3 (see FIGS. 2 and 3), an ion beam irradiation device (hereinafter referred to simply as an "irradiation device") 4, and a treatment bench 5. The particle beam therapy system 1 is practically used as a cancer treatment system. The ion beam generator 2 includes an ion source (not shown), a pre-stage accelerator 7, and a synchrotron 8. Ions (e.g., protons or carbon ions) generated in the ion source are accelerated by the pre-stage accelerator 7 (e.g., a linear accelerator). The accelerated ion beam is introduced from the pre-stage accelerator 7 to the synchrotron 8 through a low-energy beam line 6. In the illustrated example, a proton beam is used as the ion beam. The ion beam in the form of the proton beam is further accelerated in the synchrotron 8 to have a set level of energy (usually 100-200 Mev). Thereafter, the ion beam is extracted through an extraction deflector 9.

The ion beam extracted from the synchrotron 8 reaches the irradiation device 4 through a high-energy beam line 10. The irradiation device 4 and an inverted U-shaped beam transport 11 as a part of the high-energy beam line 10 are mounted to a gantry barrel 18 (see FIG. 2) of the rotating gantry 3 and are rotated with rotation of the rotating gantry 3. The ion beam passes through the beam transport 11 and is irradiated from a snout 4a (see FIGS. 4 and 5) of the irradiation device 4 to an affected part 15 (see FIG. 4) in the body of a patient 14 who is lying on a treatment couch (hereinafter referred to simply as a "couch") 13 set on the treatment bench 5.

Figure 2:
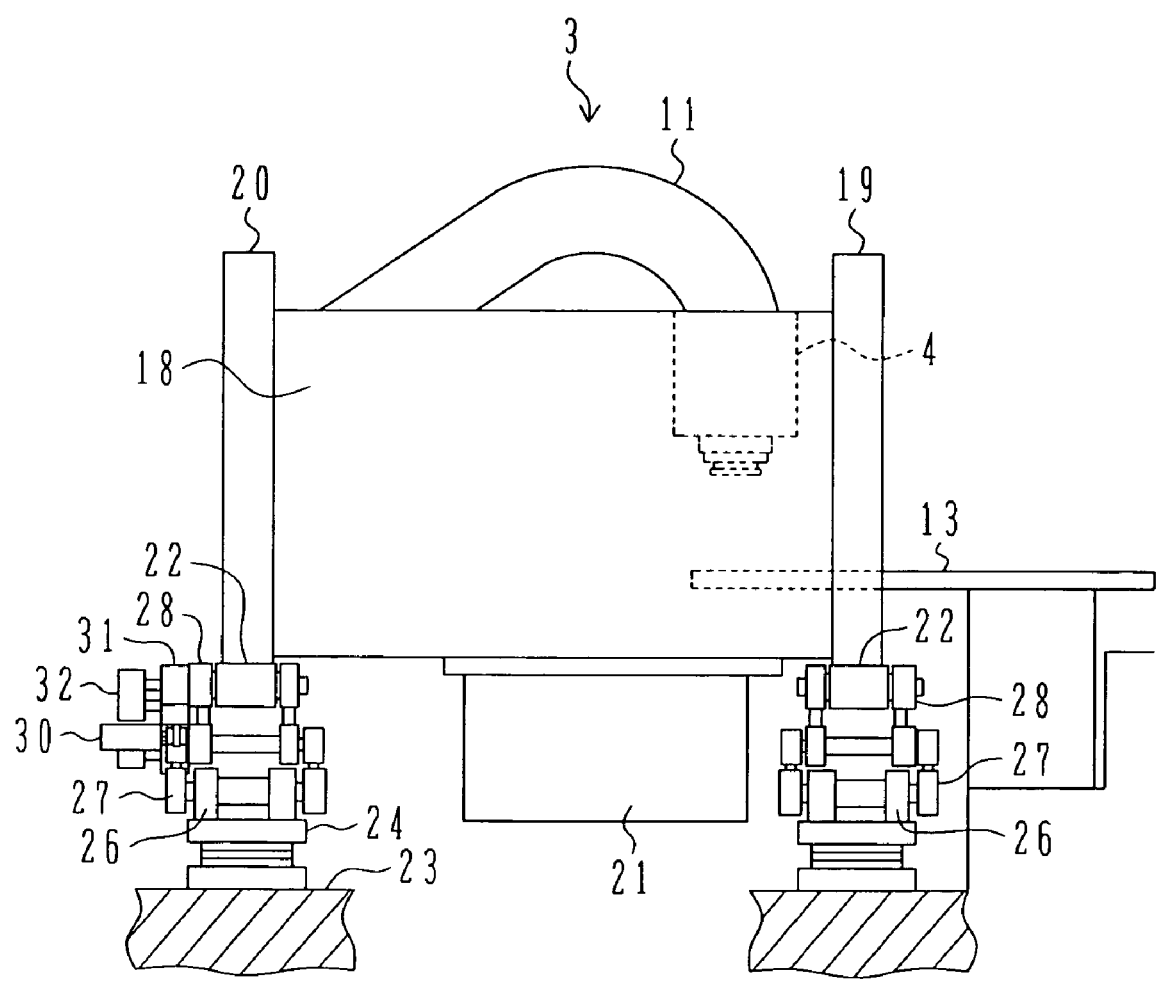
FIG. 2 is a side view showing the overall structure of the rotating gantry included the particle beam therapy system shown in FIG. 1.
Figure 3:
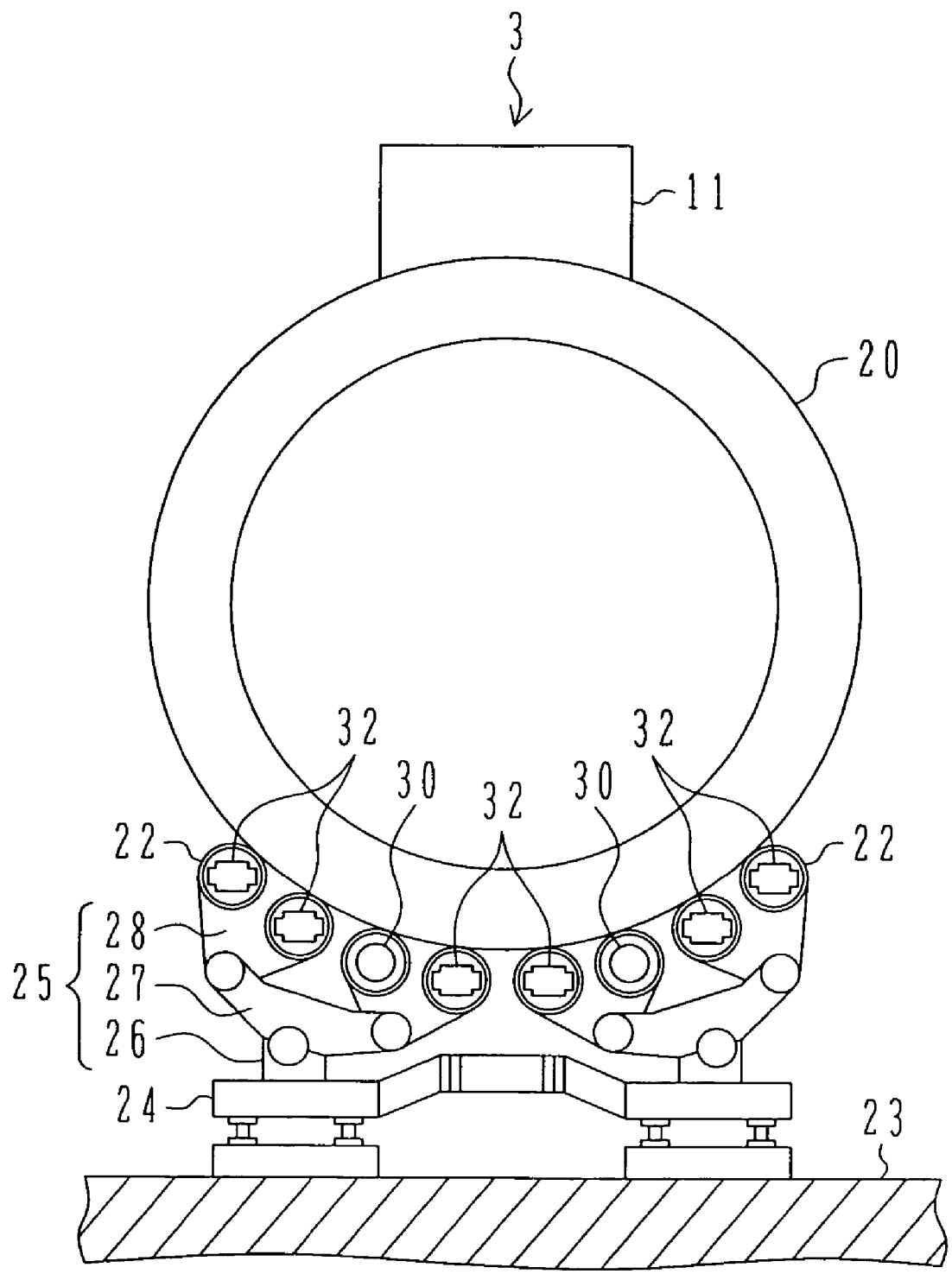
FIG. 3 is an elevational view of the rotating gantry shown in FIG. 2 as viewed from the rear side.

As shown in FIGS. 2 and 3, the rotating gantry 3 comprises a substantially cylindrical gantry barrel 18, a front ring (ring member) 19 provided at an end of the gantry barrel 18 on the front side (on the same side as a treatment chamber or on the right side in FIG. 2), and a rear ring (ring member) 20 provided at a rear-side end of the gantry barrel 18. Since the gantry barrel 18 is of the cylinder structure, it has larger rigidity and higher irradiation accuracy than those of the above-described known rotating gantry which includes the gantry barrel made up of the plurality of braces and the reinforcing members of the truss structure. The gantry barrel 18 includes therein a treatment cage 16 (see FIGS. 4 and 5) in which the ion beam is irradiated to the affected part 15 in the body of the patent 14. The irradiation device 4 for irradiating the ion beam, which has been transported through the inverted U-shaped beam transport 11, to the patient 14 is disposed inside the treatment cage 16. The irradiation device 4 is mounted to the gantry barrel 18. Around the gantry barrel 18, there are disposed the inverted U-shaped beam transport 11, a counterbalance weight 21 positioned on the opposed side to the irradiation device 4 and keeping the rotation of the rotating gantry 3 in balance, etc.

The front ring 19 and the rear ring 20 are each supported by a plurality of rotatable support rollers (rollers) 22. The plurality of support rollers 22 are rotatably mounted to link frames (roller support members) 25 which are provided on supports (pedestals) 24 installed on a building base 23. Each of the link frames 25 is made up of a bracket 26 mounted to the support 24, a parent link member 27 rotatably mounted to the bracket 26, and two child link members 28 rotatably mounted to the parent link member 27. The link frames 25 are structured such that the plurality of support rollers 22 are arranged along outer peripheral (circumferential) surfaces of the front ring 19 and the rear ring 20. More specifically, in this embodiment, one support 24 is installed for each of the front and rear sides of the rotating gantry 3. Two link frames 25 are provided on the one support 24. The front ring 19 and the rear ring 20 are each supported by eight support rollers 22 which are in turn supported by the two link frames 25.

Gantry rotating motors 30 are connected respectively to two of the eight support rollers 22 arranged on the rear side through reduction gears (not shown). The rotating gantry 3 is rotated by torque of the gantry rotating motors 30 transmitted through friction between the rear ring 20 and the support rollers 22. Also, brakes 31 are connected to the remaining six of the eight support rollers 22 arranged on the rear side. The brakes 31 are each constructed such that when the rotating gantry 3 is driven for rotation, air is supplied to the brake to release braking forces applied to the support rollers 22, and in the event of emergency stop, the air is discharged to apply the braking forces to the support rollers 22. The braking forces are transmitted to the rear ring 20 through the friction between the rear ring 20 and the support rollers 22, whereby the rotating gantry 3 is stopped. The supply and discharge of the air to the brakes 31 are switched over by solenoid valves 32. When the solenoid valves 32 are closed, the air supplied to the brakes 31 is sealed therein, and when they are opened, the air is discharged from the brakes 31 (as described in detail later).

In this embodiment, the two support rollers 22 to which connected are the gantry rotating motors 30 and the six support rollers 22 to which connected are the brakes 31 are arranged in bisymmetrical relation, as viewed in the axial direction of the rotating gantry 3, so that the torque from the gantry rotating motors 30 and the braking forces from the brakes 31 are transmitted to the rotating gantry 3 in a well balanced manner. Further, the gantry rotating motors 30, the brakes 31, and the solenoid valves 32 are arranged on the rear side of the rotating gantry 3 away from the treatment cage16. That arrangement is adapted for not only maintenance, but also an increase of total size of the brakes due to power-up of the brake performance which is possibly planned in future.

The rotating gantry 3 is driven and controlled for rotation by, e.g., a medical engineer 34 who operates a pendant switch 33 disposed on the building side.

Figure 4:
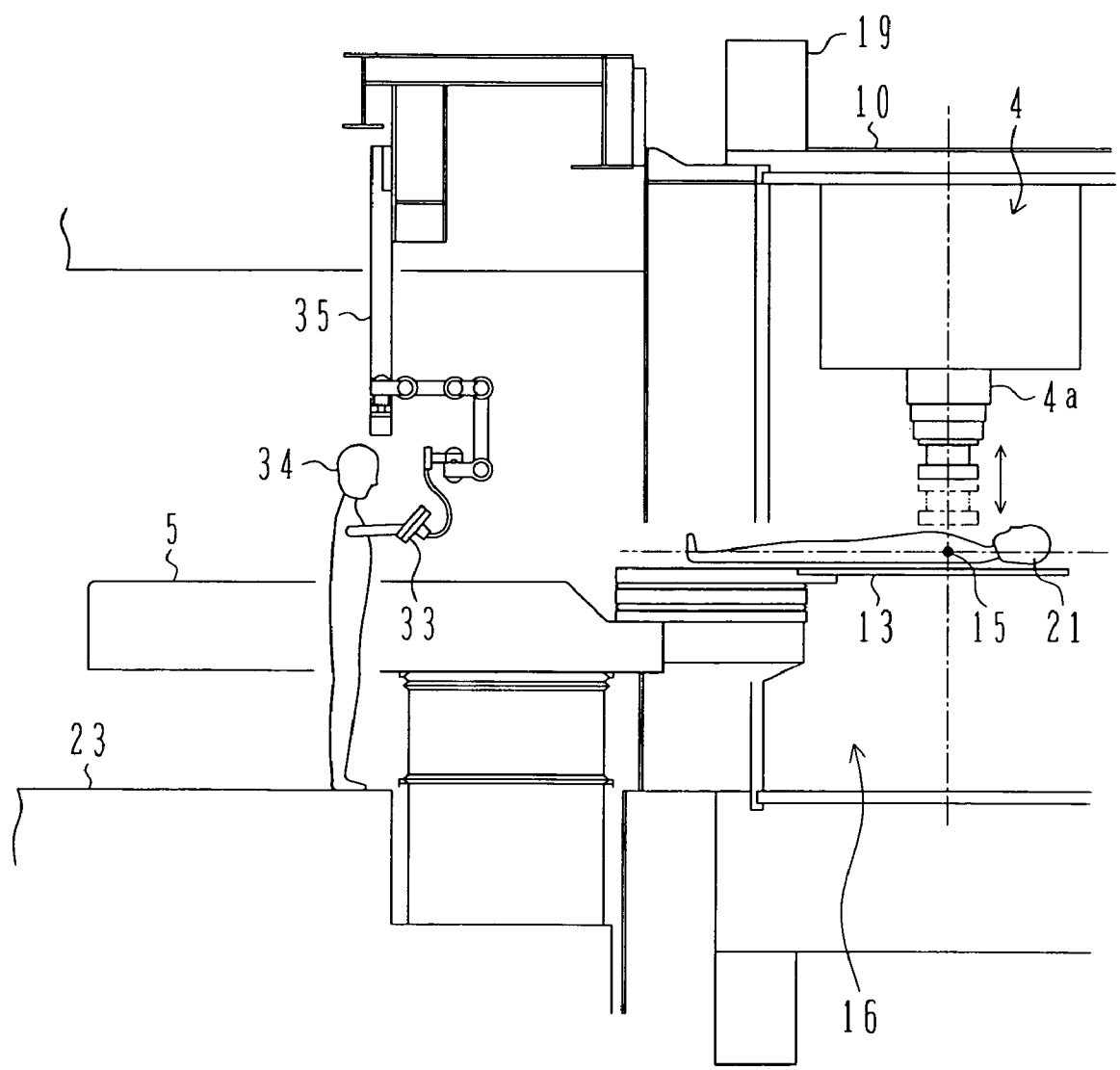
FIG. 4 is a side view of the rotating gantry, the view showing a state where a medical engineer is operating a pendant switch.
Figure 5:
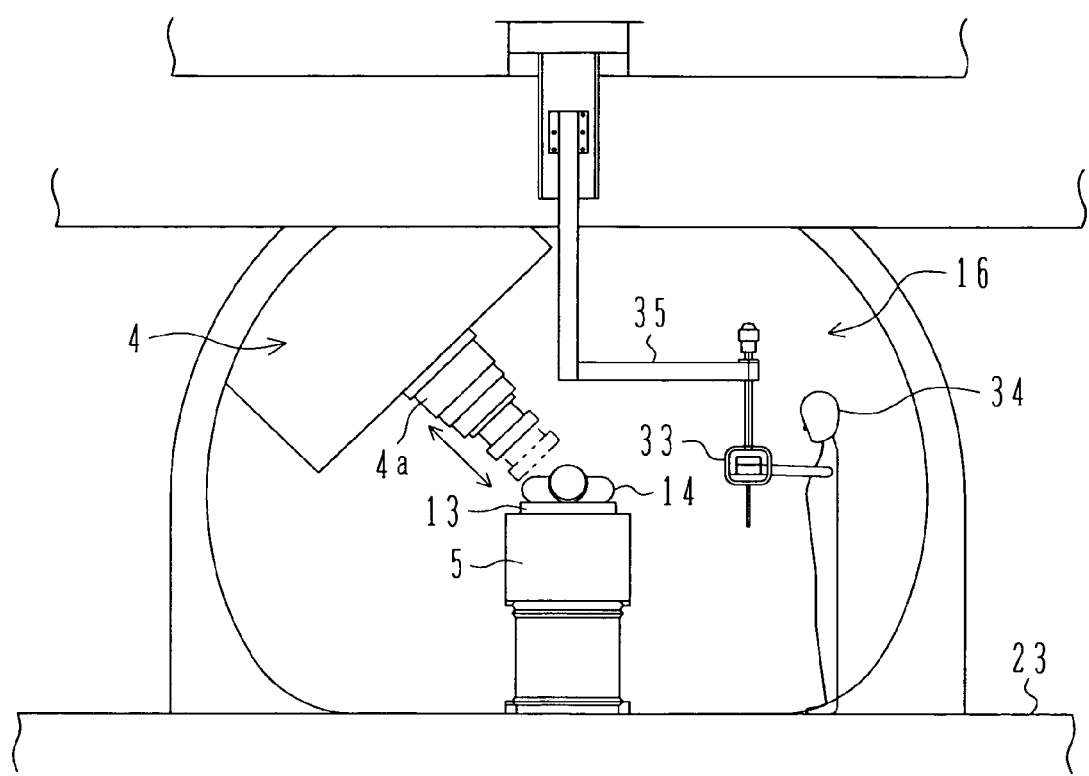
FIG. 5 is an elevational view of the rotating gantry as viewed from the rear side, the view showing the state where the medical engineer is operating the pendant switch.

As shown in FIGS. 4 and 5, the treatment 5 is mounted to the building base 23. The couch 13 on the treatment bench 5 is moved by a driver for the treatment bench 5 such that the patient 14 on the couch 13 is positioned in alignment with an axis of rotation of the rotating gantry 3. When the medical engineer 34, for example, operates the pendant switch 33 suspended from a support 35 on the front side of the rotating gantry 3, the rotating gantry 3 is rotated around the patient 14 lying on the couch 13. In such a way, the irradiation device 4 is set to orient toward the patient 14 from a predetermined direction. Accordingly, the ion beam formed by the irradiation device 4 in match with a desired irradiation field can be irradiated to the affected part from the predetermined direction. Further, a snout 4a extensible toward or contractible away from the patient 14 is disposed at a tip of the irradiation device 4, and the length of the snout 4a is adjusted so that the ion beam can be irradiated in match with individual patients. The movement of the couch 13, the rotation of the rotating gantry 3, the extension/contraction of the snout 4a, etc. are performed in accordance with treatment plan information. The positioning of the patient 14 is thus completed. Incidentally, the extension/contraction of the snout 4a is under interlock control such that the snout 4a cannot be operated unless the rotating gantry 3 and the couch 13 are stopped.

Figure 6:
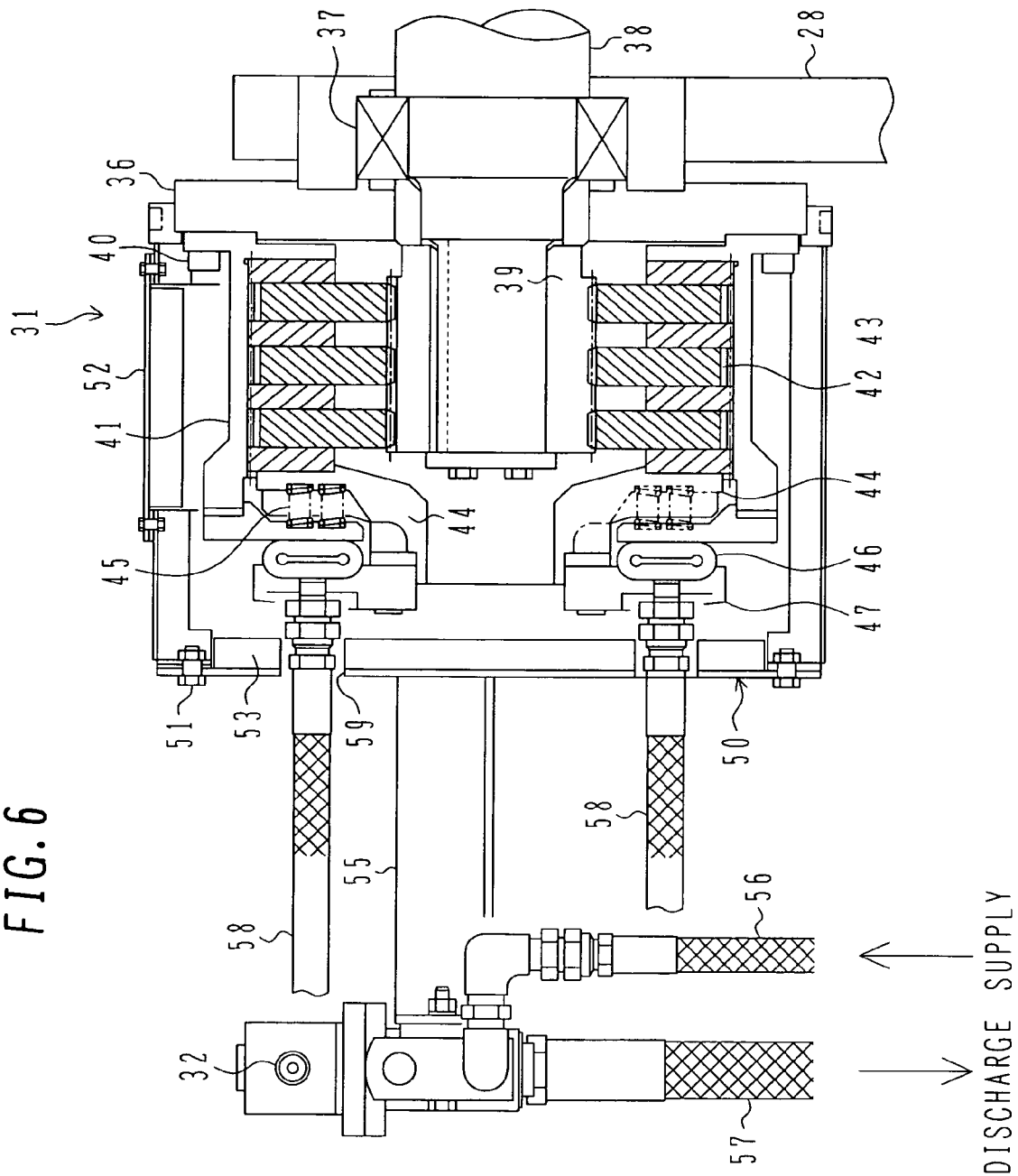
FIG. 6 is a partial sectional view showing the detailed structure a brake and a solenoid valve in a partly sectioned way.
Figure 7A:
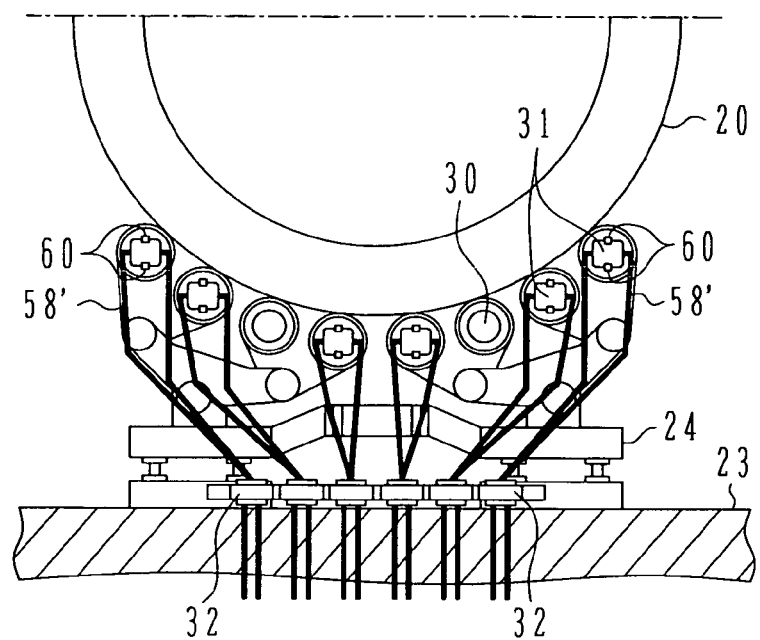
FIGS. 7A to 7D are side views and elevational views of a section including the brakes and the solenoid valves, the views comparatively showing the structure of a comparative example and the structure of the embodiment.
Figure 7B:
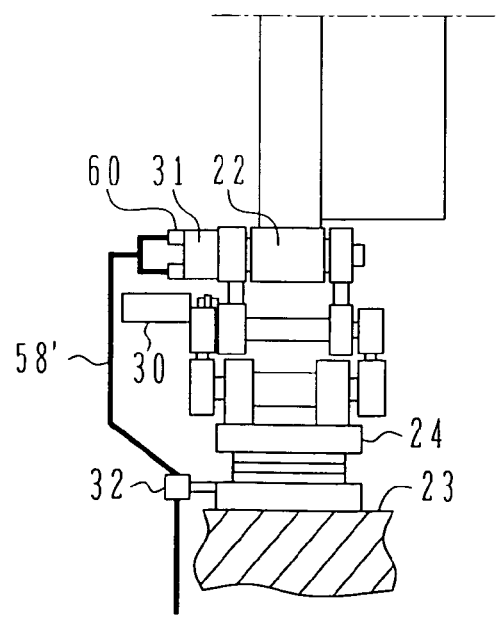
Figure 7C:
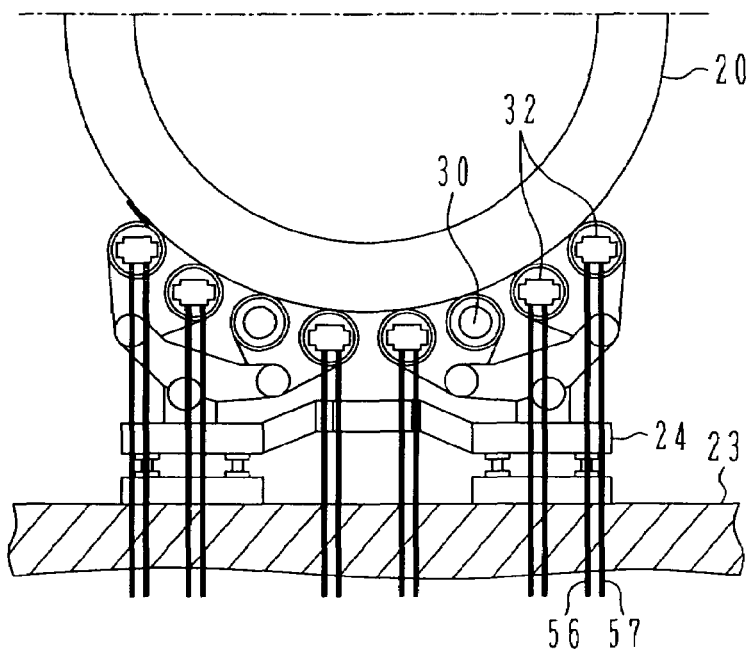
Figure 7D:
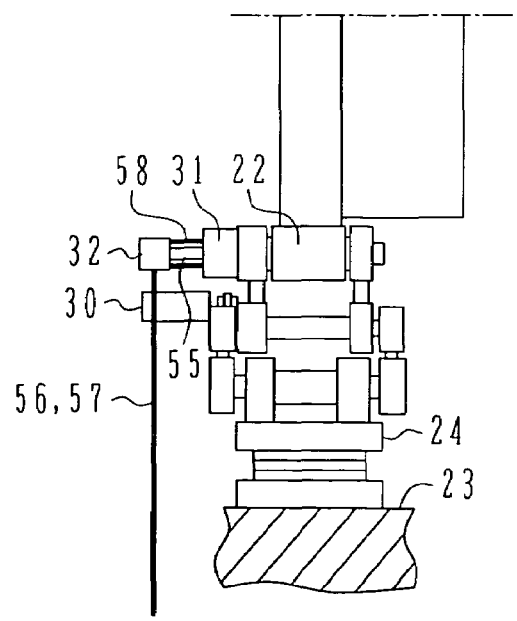

As shown in FIG. 6, each of the brakes 31 is made up of a brake support member 36, a hub 39, a disk support member 41, gears (gear members) 42, annular friction disks 43, an annular rubber tube (airbag) 46, and a rubber tube support member 47. The brake support member 36 is directly fixed to the child link member 28 of the link frame 25. The hub 39 is in the form of a spline shaft that is rotatably supported by the child link member 28 through a bearing 37 and is directly fixed to a roller shaft 38 of the support roller 22, which penetrates through the brake support member 36. The hub 39 has teeth formed on its outer peripheral surface. The disk support member 41 has a substantially cylindrical shape and is fixed to the brake support member 36 by bolts 40 while supporting the later-described friction disks 43 at the inner peripheral side thereof. Further, the disk support member 41 has teeth formed on its inner peripheral surface. The gears 42 are meshed with the teeth on the outer peripheral surface of the hub 39 and are provided in plural in the circumferential direction and in three stages in the axial direction of the roller shaft 38. The friction disks 43 are supported by the disk support member 41 at the inner peripheral side thereof and are arranged so as to sandwich the gears 42. Springs 45 press the friction disks 43 through a pressing member 44 such that the friction disks 43 press the gears 42 while sandwiching them. The rubber tube 46 is expanded with supply of air to move the pressing member 44 toward the side away from the gears 42 (i.e., toward the left in FIG. 6) against biasing forces of the springs 45, thereby releasing the pressing forces applied from the friction disks 43 to the gears 42. The rubber tube support member 47 is fixed to the pressing member 44 and support the rubber tube 46.

Further, the brake 31 includes a sound-insulating cover (cover member) 50 fixed to the brake support member 36 and disposed in surrounding relation to the components of the brake 31 (such as the hub 39, the disk support member 41, the gears 42, the friction disks 43, the pressing members 44, the springs 45, and the rubber tube 46). The sound-insulating cover 50 is made up of a steel plate (reinforcing member) 52 which is divided into a plurality of pieces and is formed so as to cover the whole of the brake 31 when the plural pieces are fixed to the brake support member 36 and joined with each other by, e.g., bolts 51, and a sound-insulating material (or a sound-absorbing material in some cases) 53 which is disposed at the inner peripheral side of the steel plate 52 to reduce noises generated by the brake 31. The steel plate 52 is provided to provide strength enough for supporting a solenoid valve support member (support) 55 in a cantilevered manner, which in turn supports the solenoid valve 32 (described in detail below). Accordingly, the steel plate 52 is not an essential material and may be replaced with a reinforced plastic material, for example, so long as the material has required strength. In addition, because the steel plate 52 is disposed to cover the whole of the brake 31, it serves not only as the reinforcing member, but also to further enhance the sound-insulating effect of the sound-insulating material 53.

The solenoid valve 32 is supported by the solenoid valve support member 55 which is attached to the steel plate 52 of the sound-insulating cover 50 so as to project in the direction away from the support roller 22 (to the left in FIG. 6). It can be therefore said that the solenoid valve 32 is supported by the child link member 28 through the brake support member 36 directly mounted to the child link member 28 of the link frame 25, the sound-insulating cover 50, and the solenoid valve support member 55.

A supply line 56 for supplying air and a discharge line 57 for discharging air are connected to the solenoid valve 32. Supply and discharge ports (not shown) of the solenoid valve 32 are directly connected to the rubber tube 46 of the brake 31 by a flexible hose 58 having proper flexibility without any valve device, e.g., a quick discharge valve, interposed between them. The flexible hose 58 is connected to one or more appropriate points (two in this embodiment) of the rubber tube 46 while passing a through-hole 59 formed in the sound-insulating cover 50 for the passage of the flexible hose 58. In this embodiment, the discharge line 57 is also formed of a flexible hose for the purpose of damping shocks applied to the discharge line 57 upon a large amount of air flowing into the line when discharged. The supply line 56 may be formed of either a steel pipe or a flexible hose.

With the structure described above, when the rotating gantry 3 is driven for rotation, the solenoid valve 32 is opened to communicate the supply line 56 and the flexible hoses 58 with each other, and the air supplied through the supply line 56 is introduced to the rubber tube 46 through the flexible hoses 58. The expanded rubber tube 46 moves the pressing member 44 in the direction away from the link frame 25 (to the left in FIG. 6) against the biasing forces of the springs 45. As a result, gaps are generated between the friction disks 43 and the gears 42, thus releasing the braking force applied to the roller shaft 38. At this time, the solenoid valve 32 is closed and the air is sealed in the flexible hoses 58 and the rubber tube 46 to hold the state where the braking force applied to the roller shaft 38 is released. The air is supplied and sealed under pressure not lower than a specified level sufficient for causing the pressing member 44 to be moved in the direction away from the gear side against the biasing forces of the springs 45.

On the other hand, when the rotating gantry 3 is stopped in the event of emergency stop, for example, the solenoid valve 32 is opened to communicate the discharge line 57 and the flexible hoses 58 with each other, and the air sealed in the flexible hoses 58 and the rubber tube 46 is discharged. Responsively, the pressing member 44 is moved in the direction toward the link frame 25 (to the right in FIG. 6) by the biasing forces of the springs 45, and each gear 42 is pressed by the friction disks 43 on both sides. As a result, the braking force applied to the roller shaft 38.

When the rubber tube 46 is expanded and contracted with the supply and discharge of air as described above, the rubber tube support member 47 is moved in the axial direction (to the left and right in FIG. 6) of the roller shaft 38. However, such movements of the rubber tube support member 47 can be absorbed because the solenoid valve 32 and the rubber tube 46 are connected by the flexible hoses 58 having proper flexibility.

The length of each flexible hose 58 has to be set in consideration of the lengths of parts (e.g., fittings, a hose itself and couplings, though not specifically shown) constituting the flexible hose 58, and the hose length enough to provide a predetermined radius of curvature not imposing external forces upon the solenoid valve 32 and the brake 31. Thus, the length of the flexible hose 58 is decided depending on those physical conditions and is usually in the range of about 0.4-1.0 m. In other words, the length of the flexible hose 58 is set at 1.0 m or less. In this embodiment, it is set to about 0.6 m (see FIG. 9B). Also, the size (diameter) of the flexible hose 58 is set to ¾ inch (see FIG. 9B). Note that the length and diameter of the flexible hose 58 are not limited to the above values and the hose length, for example, may be further shortened if possible while satisfying the aforesaid physical conditions.

In addition, the inventors studied the diameter of the discharge line 57. More specifically, the inventors prepared a system model (described in detail later) shown in FIG. 9B and computed the relationship between the line diameter and the air discharge time by using the theoretical formula for adiabatic change on an assumption that the air sealed in the flexible hoses 58 extending from the rubber tube 46 in the brake 31 to the solenoid valve 32 was all released to the atmosphere. On that occasion, the most effective diameter was sought in view of that the air discharge time is cut by increasing the line diameter, but cost efficiency is reduced if the line diameter is increased in excess of a necessary value. As a result of the computation, the effect of cutting the air discharge time was confirmed by increasing the line diameter up to 1.25 inch, but the effect was saturated with the line diameter of 1.25 inch or larger. For that reason, the diameter of the discharge line 57 was set to 1.25 inch in this embodiment.

The operation of the rotating gantry 3 of the particle beam therapy system, according to this embodiment, will be described below.

When starting the treatment irradiation for the patient 14, the couch 13 on which the patient 14 is lying, is first moved to a predetermined position inside the treatment cage 16 of the rotating gantry 3. This movement of the couch 13 is performed in accordance with the treatment plan by, e.g., the medical engineer 34 operating the pendant switch 33. After performing rough positional adjustment in such a manner, X-ray photographs of the affected part 15 in the body of the patient 14 and thereabout are taken in the direction of advance of the ion beam and the direction perpendicular to the former. The taken X-ray images are compared by a control unit (not shown) with tomographic images prepared from X-ray CT images which were taken in advance at the time of planning the treatment plan, thereby computing deviations of the coordinates. The couch 13 is moved again for close position adjustment so as to eliminate those deviations.

Then, the medical engineer 34, for example, operates the pendant switch 33 to rotate the rotating gantry 3 for positioning the irradiation device 4 such that the ion beam can be irradiated to the affected part 15 in accordance with the irradiation angle decided in the treatment plan. Also, the snout 4a is extended or contracted for adjustment to a proper length.

After completion of the positioning of the couch 13, irradiation start is instructed from a console installed in a treatment control room (not shown). In accordance with the instruction, the ion beam generated in the ion source is accelerated by the pre-accelerator 7 and enters the synchrotron 8. The ion beam accelerated by the synchrotron 8 to have energy increased to the set level is extracted from the synchrotron 8 and reaches the irradiation device 4 through the high-energy beam line 10. Then, the ion beam is irradiated from the snout 4a of the irradiation device 4 to the affected part 15 in the body of the patient 14 lying on the couch 13.

In the above-described preparatory operation prior to start of the treatment irradiation for the patient 14, the emergency stop has to be performed, for example, if the irradiation device is about to contact, e.g., the snout 4a of the irradiation device 4 or the couch 13, on which the patient 14 is lying, during the rotation of the rotating gantry 3, or if the condition of the patient 14 is abruptly changed. The emergency stop is performed by, e.g., the medical engineer 34 operating the pendant switch 33. In the emergency stop operation, the solenoid valve 32 is opened to communicate the discharge line 57 and the flexible hoses 58 with each other, and the air sealed in the flexible hoses 58 and the rubber tube 46 is discharged. Responsively, the pressing member 44 is moved in the direction toward the gear side (to the right in FIG. 6) by the biasing forces of the springs 45, and each gear 42 is pressed by the friction disks 43 on both sides, thus braking the rotation of the roller shaft 38. As a result, the braking forces are applied to the rotating gantry 3 from the six support rollers 22 connected to each brake 31, whereby the rotating gantry 3 is stopped.

The effects obtained with this embodiment will be described below one by one. For clear understanding of the effects, the following description is made, as needed, in comparison with comparative examples.

FIGS. 7A to 7D are side views and elevational views, looking from the rear side, of a section including the brakes and the solenoid valves of the rotating gantry, the views comparatively showing the structure of the comparative example and the structure of the embodiment. In a rotating gantry of the comparative example, as shown in FIGS. 7A to 7D, because the solenoid valves 32 are disposed on the support 24 installed on the building base 23, the length of a connection line 58' for connecting the brake 31 and the solenoid valve 32 to each other is relatively long (e.g., 3.0 m, see FIG. A9). Further, a quick discharge valve 60 for quickly discharging the air is disposed in the connection line 58'. The other structure is the same as that in this embodiment.

(1) Effect of Reducing Emergency Stop Angle of Rotating Gantry

Figure 8:
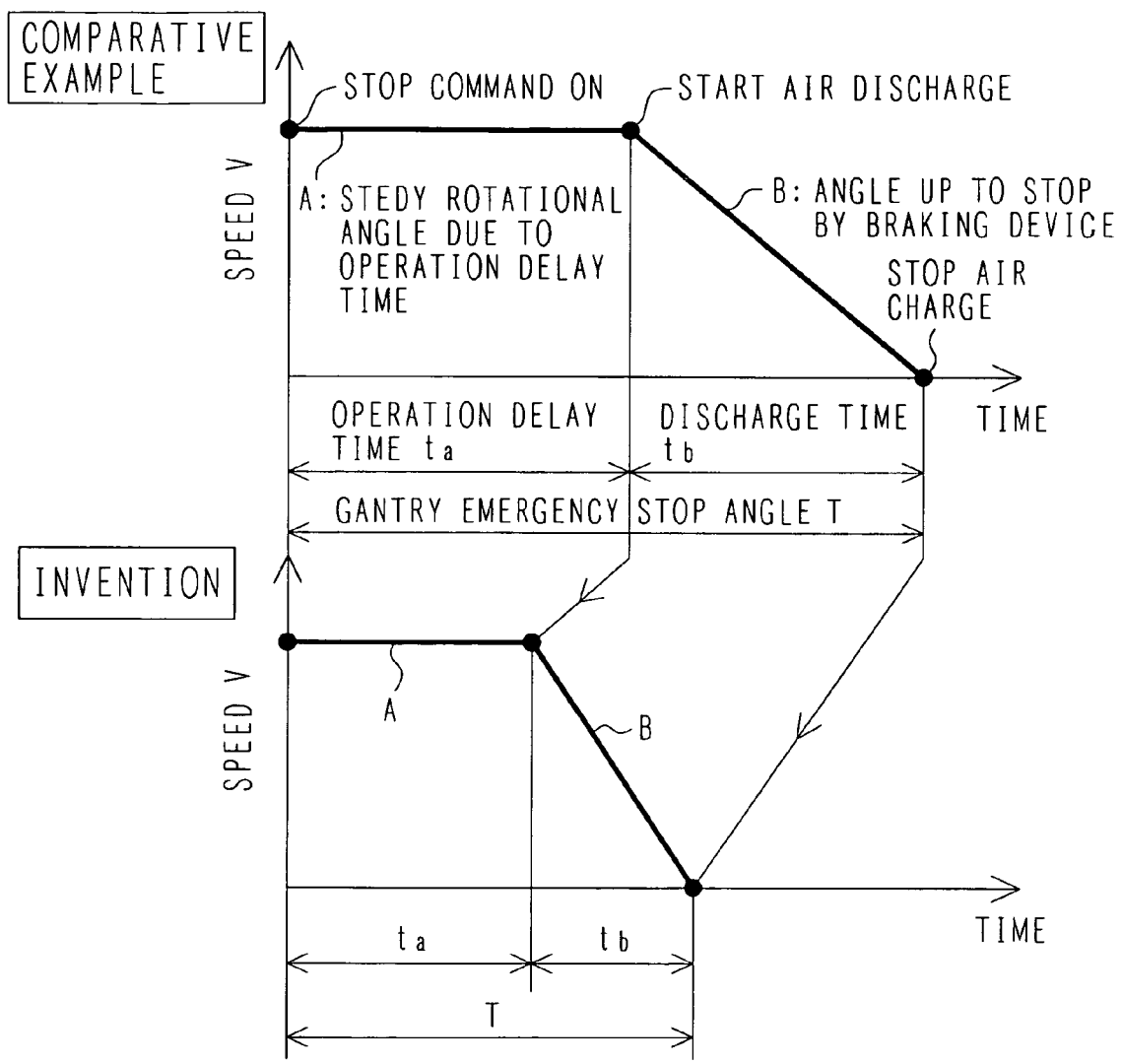
FIG. 8 is a chart for explaining the definition of an emergency stop angle of the rotating gantry.

The term "emergency stop angle of the rotating gantry" means a rotational angle of the rotating gantry through which the rotating gantry is rotated from a time when emergency stop is instructed in a state rotating at a constant speed (e.g., 1 r/min) to a time when the braking force from each brake is applied at 100%. FIG. 8 specifically illustrates the definition of the emergency stop angle. As shown in FIG. 8, an emergency stop angle T of the rotating gantry 3 is defined as the sum of an angle through which the rotating gantry 3 is constantly rotated during an operation delay time ta until the air actually starts to be discharged after an emergency stop switch on the pendant switch 33 has been operated by the medical engineer 34, for example, and an angle through which the rotating gantry 3 is rotated during an air discharge time tb from the start of actual discharge of the air to 100%-output of the braking torque from the brake 31 upon completion of the air discharge.

According to this embodiment, as shown in FIG. 8, the operation delay time ta and the air discharge time tb can be both cut from those in the comparative example. As a result, the emergency stop angle T of the rotating gantry 3 can be greatly reduced. Points contributing to the effect of reducing the emergency stop angle T will be described below one by one.

(i) Effect of Reducing Emergency Stop Angle Resulting from Providing Solenoid Valve near Brake Generally, it is discussed based on the theoretical formula for adiabatic change that the air discharge time is proportional to the quotient of the volume of the sealed air by the effective cross-sectional area of parts constituting the discharge line. In other words, by reducing the volume of the sealed air, the air discharge time can be cut in proportion.

In this embodiment, as described above, the solenoid valve 32 is supported by the solenoid valve support member 55 attached to the sound-insulating cover 50 of the brake 31, and the sound-insulating cover 50 is attached to the brake support member 36 directly mounted to the child link member 28 of the link frame 25. With that structure, the solenoid valve 32 can be disposed just near the brake 31, and hence the length of the flexible hose 58 connecting the solenoid valve 32 and the brake 31 (specifically, the rubber tube 46) can be minimized. Accordingly, the amount of air sealed between the brake 31 and the solenoid valve 32, i.e., the absolute amount of air to be discharged, can be reduced and the air discharge time tb can be cut. As a result, the emergency stop angle T of the rotating gantry 3 can be reduced.

Figure 9A:
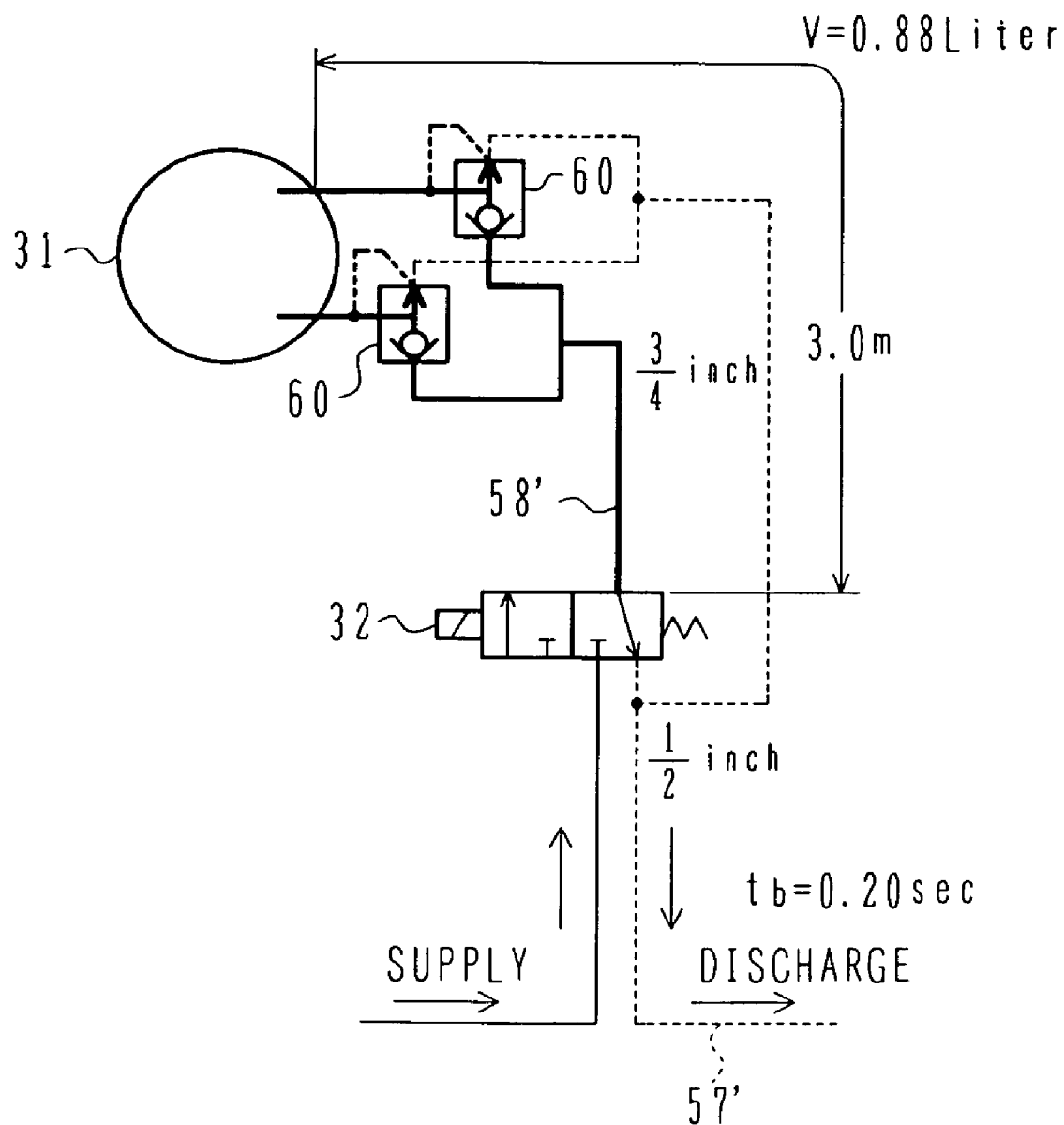
FIGS. 9A and 9B are diagrams showing system models of the comparative example and the embodiment, which were prepared for studying sizes (diameters) of discharge lines.
Figure 9B:
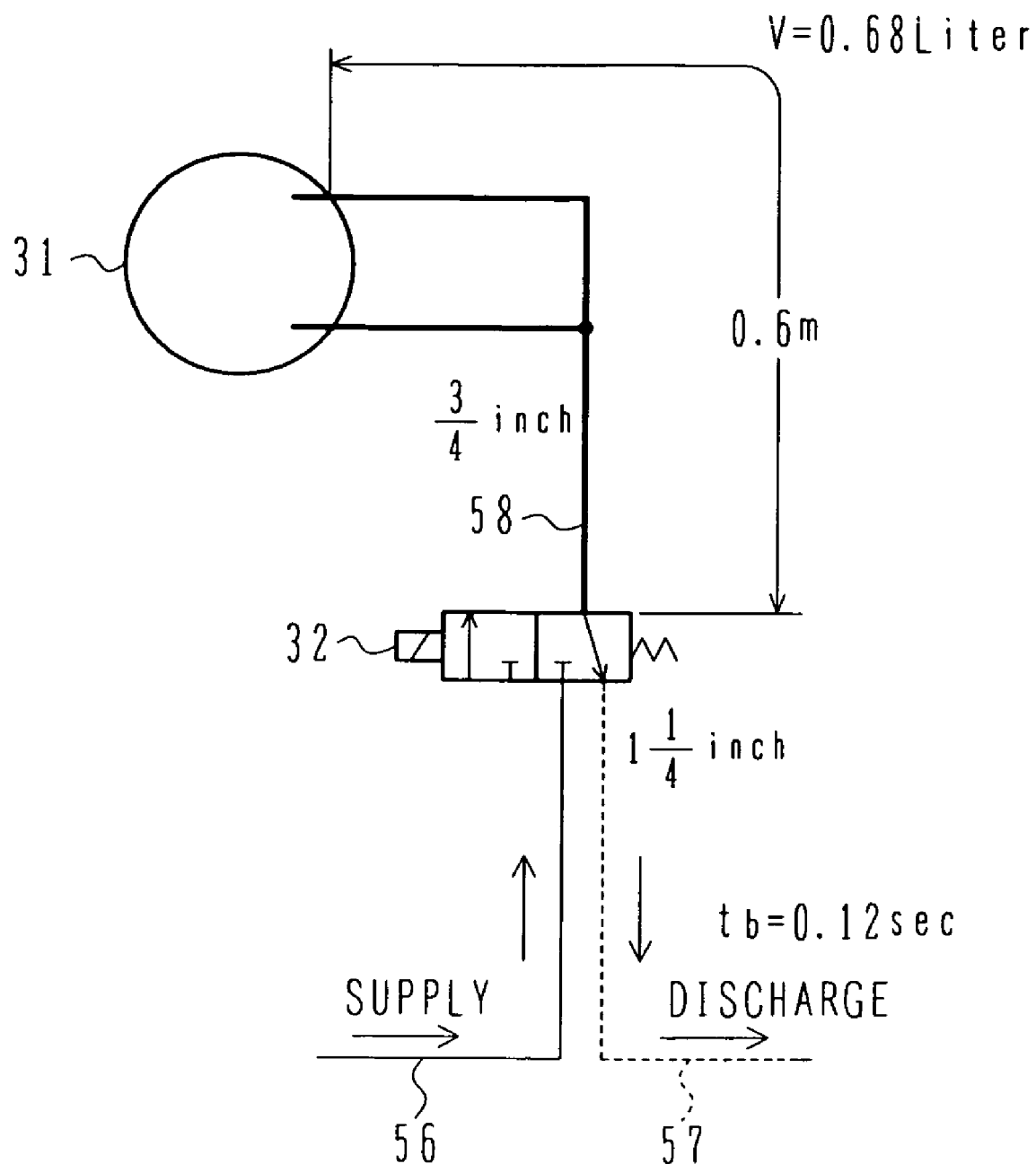

(ii) Effect of Reducing Emergency Stop Angle Resulting from Optimizing Diameter of Discharge Line As described above, the inventors prepared the system model for the diameter of the discharge line 57 and studied the relationship between the line diameter and the air discharge time by using the theoretical formula for adiabatic change. As a result, the effect of cutting the air discharge time was confirmed by increasing the line diameter up to 1.25 inch, but the effect was saturated with the line diameter of 1.25 inch or larger. For that reason, the diameter of the discharge line 57 was set to 1.25 inch in this embodiment. FIGS. 9A and 9B show the system models of the comparative example and the embodiment, which were prepared for studying the diameters of respective discharge lines. In the comparative example, the length and diameter of the line 58' connecting the brake 31 and the solenoid valve 32 were 3.0 m and ¾ inch, respectively, and the diameter of a discharge line 57' was ½ inch. In this case, the amount of air sealed in the line 58' was 0.88 L and the air discharge time tb was computed as 0.20 sec based on the theoretical formula for adiabatic change. In contrast, according to this embodiment, because of the structure enabling the solenoid valve 32 to be disposed just near the brake 31 as described above in (i), it was possible to shorten the length of the flexible hose 58 connecting the brake 31 and the solenoid valve 32 to, e.g., 0.6 m. The diameter of the flexible hose 58 was the same, i.e., ¾ inch, as that in the comparative example. Further, the diameter of the discharge line 57 was set to 1.25 inch as a result of the above-mentioned studies. In this embodiment, the amount of air sealed in the flexible hose 58 was 0.68 L and the air discharge time tb was computed as 0.12 sec based on the theoretical formula for adiabatic change. From those computed results, it is understood that this embodiment is able to surely cut the air discharge time tb in comparison with the comparative example. Hence the emergency stop angle of the rotating gantry 3 can be reduced.

(iii) Effect of Reducing Emergency Stop Angle Resulting from Cutting Operation Delay Time The analysis made by the inventors shows that the operation delay time ta is primarily decided by a time taken for the air in the brake 31 and the flexible hose 58 to be actually discharged with the operation of the solenoid valve 32 which electrically controls the supply/discharge of air in response to an electric signal, and by a time until, for example, the quick discharge valve 60 used in the structure of the comparative example senses a differential pressure occurred in the line 58' connecting the brake 31 and the solenoid valve 32 and starts the operation. In this embodiment, because of the structure directly connecting the brake 31 and the solenoid valve 32 by the flexible hose 58 without including the quick discharge valve 60, one of the two factors of causing the operation delay time, i.e., the delay time caused in the operation of the quick discharge valve 60, can be made 0. This enables the operation delay time ta to be cut from that in the comparative example. As a result, the emergency stop angle T can be reduced.

The foregoing (i), (ii) and (iii) are superior points of this embodiment to the comparative example from the viewpoint of reducing the emergency stop angle. Stated another way, as shown in FIG. 8, the operation delay time ta and the air discharge time tb can be both cut from those in the comparative example, whereby the emergency stop angle T can be reduced.

In addition, this embodiment is able to enhance the effect of reducing the emergency stop angle based on the following points.

(iv) Effect of Reducing Emergency Stop Angle Resulting from Employing Flexible Hose In this embodiment, the flexible hose 58 having proper flexibility is employed as the line for connecting the brake 31 and the solenoid valve 32. The use of the flexible hose 58 reduces angularly bent portions of the line and shortens the length of the connection line connecting the brake 31 and the solenoid valve 32 in comparison with the case of employing, e.g., a steel pipe as the connection line. This contributes to cutting the air discharge time tb. Further, because the use of the flexible hose 58 reduces the angularly bent portions of the line, it is possible to reduce resistance imposed on the discharged air at bent portions of the hose, and hence to further cut the air discharge time tb. As a result, the emergency stop angle T of the rotating gantry 3 can be further reduced.

(v) Effect of Reducing Emergency Stop Angle Resulting from Employing Rubber Tube In this embodiment, the annular rubber tube 46 is included in the brake 31 and air is supplied to and discharged from the rubber tube 46, thus releasing and applying the braking force. With that structure employing contractible rubber as a material of the air bag, the rubber tube 46 develops a contractive force by itself when the air is discharged from the rubber tube 46, to thereby cut the air discharge time. Thus, the use of the rubber tube 46 also enhances the effects of cutting the air discharge time tb. Another effect resulting from using the annular rubber tube 46 is that the air volume required for operating the brake 31 can be reduced.

As seen from the above description of (i) to (v), this embodiment is able to greatly reduce the emergency stop angle of the rotating gantry 3. Accordingly, the braking time of the rotating gantry 3 can be cut. In particular, even in the case of using the cylinder structure having a larger mass like the gantry barrel 18 used in this embodiment, it is possible to brake and stop the rotating gantry 3 in a shorter time. Further, the gantry barrel 18 has substantially the cylindrical form, namely the cylinder structure, and therefore has larger rigidity. This improves the irradiation accuracy of the ion beam to the affected part of the patient body. Thus, the rotating gantry 3 can be quickly braked and stopped while maintaining high irradiation accuracy.

(2) Effect of Reducing Noises

In this embodiment, the periphery of the brake 31 is covered with the sound-insulating cover 50 made up of the steel plate 52 and the sound-insulating material 53. With that structure, it is possible to reduce noises of the brake 31, particularly noise generated when a large amount of air quickly flows from the flexible hose 58 to the discharge line 57 when the air is discharged, and noise generated when the parts of the brake 31 strike against each other or vibrate, for example. Accordingly, the noises of the brake 31 can be greatly reduced in comparison with the case of employing the structure of the comparative example in which the brake 31 is not provided with the cover.

Further, as described above in (iii), this embodiment employs the structure directly connecting the brake 31 and the solenoid valve 32 by the flexible hose 58 without including the quick discharge valve 60. In general, when the quick discharge valve is used, the quick discharge valve acts as a throttle when a large amount of air required for actuating the brake is discharged, thereby generating noise upon the passage of the air through the throttle. However, such noise can be avoided in this embodiment because of no provision of the quick discharge valve. Accordingly, this embodiment is able to further reduce noises in comparison with the rotating gantry of the comparative example. From the viewpoint of obtaining only the effect of reducing noises, one conceivable solution is to add a silencer to the structure of the comparative example. But that solution is not desired because the added components including the silencer act as resistance against the air discharged and prolong the air discharge time tb.

The foregoing is the superior point of this embodiment to the comparative example from the viewpoint of reducing noises.

In addition, this embodiment is able to further enhance the effect of reducing noises from the following feature.

In this embodiment, as described above in (i)-(iv), the flexible hose 58 having proper flexibility is used as the line for connecting the brake 31 and the solenoid valve 32, and the angularly bent portions of the line can be reduced in comparison with the case of employing a line made of a steel, for example. Stated another way, noise generated upon air striking against the angularly bent portions of the line can be reduced. This contributes to further enhancing the effect of reducing noises.

As a result of the above-described effect of reducing noises, the rotating gantry 3 of this embodiment can suppress an uncomfortable feel given to the patient by the noises.

What is claimed is:

1. A rotating gantry of a particle beam therapy system, said gantry comprising:
   a gantry barrel;
   ring members provided respectively at axial opposite ends of said gantry barrel;
   a plurality of rollers rotatably supporting said ring members;
   a roller support member for supporting said plurality of rollers;
   a brake connected to at least one of said plurality of rollers, said brake releasing a braking force applied to said one roller upon supply of air and applying the braking force to said one roller upon discharge of air;
   a solenoid valve for sealing the supplied air in said brake when closed, and discharging the air from said brake when opened; and
   a solenoid valve support member mounted to said roller support member and supporting said solenoid valve.

2. The rotating gantry of the particle beam therapy system according to claim 1, wherein said solenoid valve support member comprises a cover member attached to said roller support member and covering said brake, and a support for supporting said solenoid valve.

3. The rotating gantry of the particle beam therapy system according to claim 2, wherein said cover member comprises a sound-insulating material disposed to cover said brake, and a reinforcing member surrounding said sound-insulating material, said support being fixed to said reinforcing member.

4. The rotating gantry of the particle beam therapy system according to claim 1, wherein said roller support member includes a link frame comprising a parent link member rotatably mounted to a bracket fixed to a pedestal and two child link members rotatably mounted to said parent link member, and said solenoid valve support member is mounted to said child link member.

5. The rotating gantry of the particle beam therapy system according to claim 1, wherein said brake comprises a gear member for applying a braking force to a roller shaft of said at least one roller when pressed, a spring for pressing said gear member, and an airbag for releasing a pressing force applied from said spring to said gear member when air is supplied to said airbag.

6. The rotating gantry of the particle beam therapy system according to claim 5, wherein said airbag is made of a contractible material.

7. The rotating gantry of the particle beam therapy system according to claim 1, wherein said brake and said solenoid valve are connected to each other without any valve device interposed therebetween.

8. The rotating gantry of the particle beam therapy system according to claim 7, wherein said brake and said solenoid valve are connected to each other by a line made of a flexible material.

9. A rotating gantry of a particle beam therapy system including a treatment cage in which a charged particle beam is irradiated, said gantry comprising:
a gantry barrel;
ring members provided respectively at axial opposite ends of said gantry barrel;
a plurality of rollers rotatably supporting said ring members;
a roller support member for supporting said plurality of rollers;
a brake connected to at least one of said plurality of rollers, said brake releasing a braking force applied to said one roller upon supply of air and applying the braking force to said one roller upon discharge of air;
a solenoid valve for sealing the supplied air in said brake when closed, and discharging the air from said brake when opened; and
a solenoid valve support member mounted to said roller support member and supporting said solenoid valve.

10. A rotating gantry of a particle beam therapy system, comprising:
a gantry barrel;
ring members provided at axial opposite ends of said gantry barrel;
a plurality of rollers rotatably supporting said ring members;
a roller support member for supporting said plurality of rollers;
a brake connected to at least one of said plurality of rollers, said brake releasing a braking force applied to said one roller upon supply of air and applying the braking force to said one roller upon discharge of air; and
a solenoid valve disposed near said brake, sealing the supplied air in said brake when closed, and discharging the air from said brake when opened.

11. The rotating gantry of the particle beam therapy system according to claim 1, wherein said solenoid valve is connected to said brake through a line having a length equal to or less than 1.0 m.

12. The rotating gantry of the particle beam therapy system according to claim 3, wherein said brake is connected to each of rollers selected from said plurality of rollers, and said cover member is provided to each of said rollers to which said brake is connected.

* * * * *